US00PP26494P2

(12) United States Plant Patent
Koning

(10) Patent No.: US PP26,494 P2
(45) Date of Patent: Mar. 8, 2016

(54) ***LAVANDULA* PLANT NAMED 'ANOUK DELUXE 109'**

(50) Latin Name: *Lavandula stoechas*
Varietal Denomination: Anouk Deluxe 109

(71) Applicant: Lammert Koning, Nuis (NL)

(72) Inventor: Lammert Koning, Nuis (NL)

(73) Assignee: New Variety BV., Kudelstaart (NL)

( * ) Notice: Subject to any disclaimer, the term of this patent is extended or adjusted under 35 U.S.C. 154(b) by 90 days.

(21) Appl. No.: 14/120,159

(22) Filed: Apr. 30, 2014

(51) Int. Cl.
*A01H 5/02* (2006.01)

(52) U.S. Cl.
USPC ..... Plt./445

(58) Field of Classification Search
USPC ..... Plt./445
See application file for complete search history.

*Primary Examiner* — Susan McCormick Ewoldt
(74) *Attorney, Agent, or Firm* — C. A. Whealy

(57) ABSTRACT

A new and distinct cultivar of *Lavandula* plant named 'Anouk Deluxe 109', characterized by its compact and broadly upright plant habit; freely branching growth habit; dense and bushy appearance; durable broad leaves; freely flowering habit; violet blue and purple-colored flowers positioned on strong and erect peduncles; and good garden performance.

1 Drawing Sheet

Botanical designation: *Lavandula stoechas.*
Cultivar denomination: 'ANOUK DELUXE 109'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 109'.

The new Lavender plant is a product of a planned breeding program conducted by the Inventor in Nuis, The Netherlands. The objective of the breeding program was to develop new strong *Lavandula* plants with attractive plant form and flower coloration.

The new *Lavandula* plant originated from a cross-pollination made by the Inventor in July, 2007 of a proprietary selection of *Lavandula stoechas* identified as code number L-507, not patented, as the female, or seed, parent with *Lavandula stoechas* 'Giant', not patented, as the male, or pollen, parent. The new *Lavandula* plant was discovered and selected by the Inventor in 2009 as a single flowering plant within the progeny of the stated cross-pollination in a controlled environment in Nuis, The Netherlands.

Asexual reproduction of the new *Lavandula* plant by terminal cuttings in a controlled greenhouse environment in De Lier, The Netherlands since September, 2010 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 109' as a new and distinct *Lavandula* plant:

1. Compact and broadly upright plant habit.
2. Freely branching growth habit; dense and bushy appearance.
3. Durable broad leaves.
4. Freely flowering habit.
5. Violet blue and purple-colored flowers positioned on strong and erect peduncles.
6. Good garden performance.

Plants of the new *Lavandula* differ from plants of the female parent selection primarily in leaf size as plants of the new *Lavandula* have broader leaves than plants of the female parent selection.

Plants of the new *Lavandula* differ from plants of the male parent, 'Giant', primarily in terminal bract size as plants of the new *Lavandula* have smaller terminal bracts than plants of 'Giant'.

Plants of the new *Lavandula* can be compared to plants of the *Lavandula stoechas* 'Anouk', disclosed in U.S. Plant Pat. No. 16,685. In side-by-side comparisons, plants of the new *Lavandula* differ from plants of 'Anouk' in the following characteristics:

1. Plants of the new *Lavandula* are more compact, bushier and denser than plants of 'Anouk'.
2. Plants of the new *Lavandula* have larger and stiffer leaves than plants of 'Anouk'.

Plants of the new *Lavandula* can also be compared to plants of the *Lavandula stoechas* 'Silver Anouk', disclosed in U.S. Plant Pat. No. 20,068. In side-by-side comparisons, plants of the new *Lavandula* differ from plants of 'Silver Anouk' in the following characteristics:

1. Plants of the new *Lavandula* are more compact, bushier and denser than plants of 'Silver Anouk'.
2. Plants of the new *Lavandula* have larger and stiffer leaves than plants of 'Silver Anouk'.
3. Plants of the new *Lavandula* and 'Silver Anouk' differ in leaf color.

BRIEF DESCRIPTION OF THE PHOTOGRAPH

The accompanying photograph illustrates the overall appearance of the new *Lavandula* plant showing the colors as true as it is reasonably possible to obtain in colored reproductions of this type. Colors in the photograph may differ slightly from the color values cited in the detailed botanical description which accurately describe the colors of the new *Lavandula* plant.

The photograph comprises a side perspective view of a typical flowering plant of 'Anouk Deluxe 109' grown in a container.

DETAILED BOTANICAL DESCRIPTION

Plants used in the aforementioned photograph and following detailed description were grown in 2.3-liter containers during the early summer in a glass-covered greenhouse in Boskoop, The Netherlands and under cultural practices typical of commercial *Lavandula* production. Plants were pinched two times and were ten months old when the photograph and description were taken. During the production of the plants, day temperatures ranged from 14° C. to 26° C. and night temperatures ranged from 6° C. to 18° C. In the following description, color references are made to The Royal Horticultural Society Colour Chart, 2007 Edition, except where general terms of ordinary dictionary significance are used.

Botanical classification: *Lavandula stoechas* 'Anouk Deluxe 109'.

Parentage:

*Female, or seed, parent.*—Proprietary selection of *Lavandula stoechas* identified as code number L-507, not patented.

*Male, or pollen, parent.*—*Lavandula stoechas* 'Giant', not patented.

Propagation:

*Type.*—Terminal vegetative cuttings.

*Time to initiate roots, summer.*—About one week at temperatures ranging from 14° C. to 26° C.

*Time to initiate roots, winter.*—About ten days at temperatures ranging from 14° C. to 26° C.

*Time to produce a rooted young plant, summer.*—About three to four weeks at temperatures ranging from 14° C. to 26° C.

*Time to produce a rooted young plant, winter.*—About four to six weeks at temperatures ranging from 14° C. to 26° C.

*Root description.*—Fine, fibrous; white in color.

*Rooting habit.*—Freely branching; dense.

Plant description:

*Plant and growth habit.*—Herbaceous perennial; compact and broadly upright plant habit; freely branching habit, dense and bushy appearance; moderately vigorous growth habit; flowers arranged in verticillasters on crowded spikes with showy terminal flower bracts.

*Plant height.*—About 21.5 cm.

*Plant width.*—About 24.2 cm.

*Lateral branch description.*—Quantity per plant: About 14. Length, from stem to base of inflorescence: About 7.6 cm. Diameter: About 4 mm. Internode length: About 1 mm. Strength: Strong. Aspect: Mostly upright. Texture: Densely tomentose. Color: Close to between 143C and 145B; pubescence, close to 157C to 157D.

*Leaf description.*—Arrangement: Opposite, simple; sessile. Length: About 5 cm. Width: About 1.15 cm. Shape: Lanceolate. Apex: Acute. Base: Cuneate. Margin: Entire; very slightly revolute. Texture, upper and lower surfaces: Densely pubescent. Fragrance: Strongly aromatic, pungent. Venation pattern: Pinnate. Color: Developing leaves, upper surface: Close to 137C. Developing leaves, lower surface: Close to 138A to 138B. Fully expanded leaves, upper surface: Close to between 137A and N137A; venation, close to 144B; pubescence, close to 157C to 157D. Fully expanded leaves, lower surface: Close to 137A; venation, close to 144B to 144C; pubescence, close to 157C to 157D.

Flower description:

*Flower type, arrangement and habit.*—Small single flowers arranged in compact verticillasters on crowded spikes; freely flowering, about 320 flowers developing per inflorescence; flowers tubular with five lobes; inflorescences with showy terminal bracts.

*Natural flowering season.*—Long flowering period; continuous from late spring into the late summer in The Netherlands.

*Flower longevity on the plant.*—Individual inflorescences last about ten days on the plant; flowers not persistent.

*Fragrance.*—None detected.

*Flower buds.*—Length: About 5 mm. Diameter: About 1.5 mm. Shape: Narrowly oblong. Color: Close to 145A; apex, close to between N92A and 203A.

*Inflorescence size.*—Height: About 4.7 cm. Diameter, apex: About 1.7 cm. Diameter, base: About 1.7 cm.

*Flower size.*—Diameter: About 4 mm. Depth (height): About 8.5 mm.

*Petals.*—Quantity and arrangement: Five, fused into a tube. Length: About 8 mm. Width: About 2 mm. Shape: Roughly spatulate; lower 75% fused into a tube. Apex: Rounded. Margin: Entire. Texture, upper and lower surfaces: Smooth, glabrous. Color: When opening, upper and lower surfaces: Close to N92A; tube, close to NN155D. Fully opened, upper and lower surfaces: Close to N92C; tube, close to NN155D.

*Terminal flower bracts.*—Quantity and arrangement: About five to seven positioned at inflorescence apex. Length: About 2 cm. Width: About 8 mm. Shape: Narrowly obovate. Apex: Broadly acute. Base: Cuneate. Margin: Entire; slightly undulate. Texture, upper and lower surfaces: Smooth, glabrous. Color, upper and lower surfaces: Close to N77C and 79D; midvein, close to N187A.

*Flower bracts.*—Quantity and arrangement: Each whorl of five flowers is subtended by a single flower bract. Length: About 9 mm. Width: About 7 mm. Shape: Broadly rhomboidal. Apex: Aristate. Base: Cuneate. Margin: Entire. Texture, upper and lower surfaces: Moderately tomentose. Color, upper and lower surfaces: Close to N77B; venation, close to N186A to N186B.

*Sepals.*—Quantity and arrangement: Five, fused into a campanulate tube. Length: About 5.5 mm. Width: About 0.75 mm. Shape: Lanceolate. Apex: Acute. Margin: Entire. Texture, upper and lower surfaces: Densely tomentose. Color: When opening, upper and lower surfaces: Close to 145A. Fully opened, upper and lower surfaces: Close to 144D.

*Peduncles.*—Length: About 4.2 cm. Diameter: About 2 mm. Aspect: Mostly upright. Strength: Strong. Texture: Densely pubescent. Color: Close to 143C; distally, slightly tinged with close to N77C; pubescence, close to 157D.

*Reproductive organs.*—Stamens: Quantity per flower: Four. Filament length: About 0.5 mm. Anther shape: Reniform. Anther length: About 0.5 mm. Anther color: Close to 166B. Pollen amount: Scarce. Pollen color: Close to 12A. Pistils: Quantity per flower: One. Pistil length: About 4 mm. Stigma shape: Club-shaped. Stigma color: Close to N186A. Style length: About 3.5 mm. Style color: Close to 155C. Ovary color: Close to 143B.

*Seeds and fruits.*—Seed and fruit production has not been observed on plants of the new *Lavandula*.

Disease & pest resistance: Plants of the new *Lavandula* have not been noted to be resistant to pathogens and pests common to *Lavandula* plants.

Garden performance: Plants of the new *Lavandula* have exhibited good tolerance to rain and wind and have been observed to tolerate high temperatures about 40° C. and to be hardy to USDA Hardiness Zone 7.

It is claimed:

1. A new and distinct *Lavandula* plant named 'Anouk Deluxe 109' as illustrated and described.

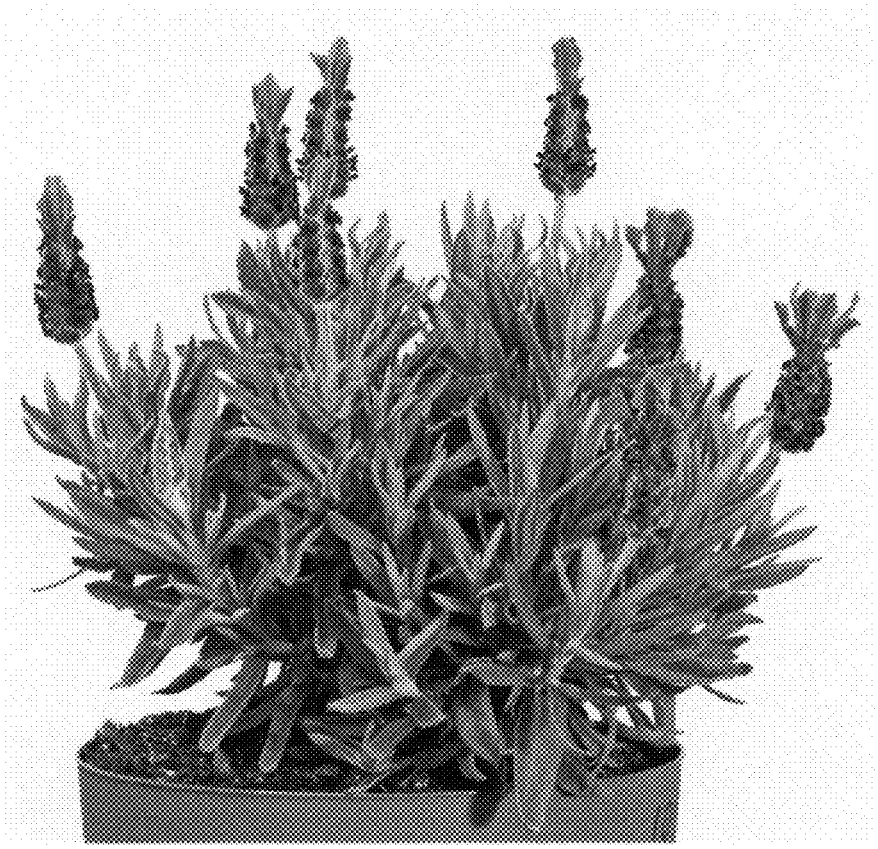

* * * * *